(12) United States Patent
Reuter

(10) Patent No.: US 7,102,016 B2
(45) Date of Patent: Sep. 5, 2006

(54) PREPARATION OF 2,2'-DI(3,4-ETHYLENEDIOXYTHIOPHENE)S

(75) Inventor: Knud Reuter, Krefeld (DE)

(73) Assignee: H. C. Starck GmbH, Gosalr (DE)

( * ) Notice: Subject to any disclaimer, the term of this patent is extended or adjusted under 35 U.S.C. 154(b) by 418 days.

(21) Appl. No.: 10/727,736

(22) Filed: Dec. 4, 2003

(65) Prior Publication Data

US 2004/0122239 A1    Jun. 24, 2004

(30) Foreign Application Priority Data

Dec. 10, 2002  (DE) ................................ 102 57 539

(51) Int. Cl.
C07D 409/00    (2006.01)
C08F 28/06     (2006.01)
C08G 75/00     (2006.01)

(52) U.S. Cl. ........................ 549/59; 526/257; 528/373
(58) Field of Classification Search .................. 549/59; 526/257; 528/373
See application file for complete search history.

(56) References Cited

U.S. PATENT DOCUMENTS

| | | | |
|---|---|---|---|
| 4,959,430 A | 9/1990 | Jonas et al. | 526/257 |
| 4,987,042 A | 1/1991 | Jonas et al. | 429/213 |
| 5,035,926 A | 7/1991 | Jonas et al. | 427/393.1 |
| 6,716,995 B1 * | 4/2004 | Huang et al. | 549/62 |
| 6,825,358 B1 * | 11/2004 | Afzali-Ardakani et al. | 549/59 |
| 6,878,801 B1 * | 4/2005 | Fujiki et al. | 528/380 |
| 6,890,715 B1 * | 5/2005 | Lewis et al. | 435/6 |
| 6,936,190 B1 * | 8/2005 | Yoshida | 252/511 |
| 6,984,737 B1 * | 1/2006 | Hartmann et al. | 549/68 |
| 2003/0052015 A1 | 3/2003 | Becker et al. | 205/414 |

OTHER PUBLICATIONS

Database CA 'Online! Chemical Abstracts Service, Columbus, Ohio, US; Zotti, Gianni et al: "Electrochemical and chemical synthesis and characterization of sulfonated poly(3,4-ethylenedioxythiophene): a novel water-soluble and highly conductive conjugated oligomer" retrived from STN Database accession No. 138:107475 XP002267046 "Zusammenfassung" & Macromolecular Chemistry and Physics (2002), 203(13), 1958-1964.

Zotti et al: "Mono—and multilayers of oligoethylene oxide-modified poly(3,4-ethylenedioxythiophene) on ITO and glass surfaces" Chem. Mater., Bd. 15, 20. Mai 2003 (May 20, 2003), Seiten 2222-28, XP002267044.

Akoudad et al: "Electrochemical Synthesis of Poly(3,4-thylenedioxythiophene) from a Dimer Precursor" Synthetic Metals, Bd. 93, Nr. 2, 1998, Seiten 111-114, XP002267045.

Sotzing G A et al: "Poly(3,4-Ethylenedioxythiopene) (Pedot) Prepared Via Electrochemical Polymerization of Edot, 2,2'-Bis (3,4'-Ethylenedioxythiophene) (Biedot), and their IMS Derivatives" Advanced Materials, VCH Verlagsgesellschaft, Weinheim, DE, Bd. 9, Nr. 10, 8. Aug. 8, 1997, Seiten 795-798, XP000695455.

Patent Abstracts of Japan vol. 2000, No. 7, Sep. 29, 2000 & JP 2000 106223 A (Fuji Photo Film Co Ltd), Apr. 11, 2000.

Cao, Jie et al: "Synthesis and Characterization of Bis(3,4-ethylenedioxythiophene)-(4,4'-dialkyl-2,2'-bithiazole) Co-oligomers for Electronic Applications" Chemistry of Material (2003), 15(2), 404-411, XP002267109.

A. Donat-Bouillud, I. Levesque, Y. Tao, M. D'Iorio, S. Beaupre, P. Blondin, M. Ranger, J. Bouchard and M. Leclerc, Chem Mater. (month unavailable) 2000, 12, p. 1931-1936 "Light-Emitting Diodes from Fluorene-Based π-Conjugated Polymers".

G.A. Sotzing, J.R. Reynolds and P.J. Steel, Adv. Mater. (month unavailable) 1997, 9(10), p. 795-798, "Poly(3,4-ethylenedioxythiophene) (PEDOT) Prepared via Electrochemical Polymerization of EDOT, 2,2'-Bis(3,4-ethylenedioxythiophene) (BiEDOT), and Their TMS Derivatives".

A.K. Mohanakrishnan, A. Hucke, M.A. Lyon, M. V. Lakshmikantham and M.P. Cava, Tetrahedron 55 (month unavailable) (1999) p. 11745-11754, "Functionalization of 3,4-Ethylenedioxythiophene".

S.S. Zhu and T.M. Swager, J. Am. Chem. Soc. (month unavailable) 1997, 119, p. 12568-12577, "Conducting Polymetallorotaxanes: Metal Ion Mediated Enhancements in Conductivity and Charge Localization".

Houben-Weyl, Methoden der Organischen Chemie 4th ed., vol. E 6a (Hetarenes I, part 1), "Thiophenes" (author: W.-D. Rudorf), p. 370-388, Sections 3.3 to 3.8.

L. Groenendaal, F. Jonas, D. Freitag, H. Pielartzik and J.R. Reynolds, Adv. Mater. (month unavailable) 2000, 12(7), p. 481-494, "Poly(3,4-ethylenedioxythiophene) and Its Derivatives: Past, Present, and Future".

* cited by examiner

Primary Examiner—Deborah C. Lambkin
(74) Attorney, Agent, or Firm—Joseph C. Gil

(57) ABSTRACT

The invention relates to a process for preparing compounds of the general formula (I)

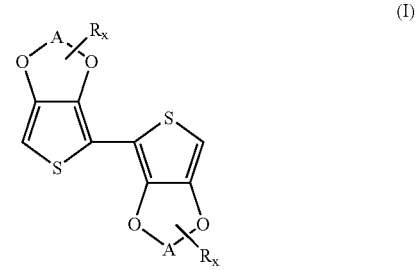

(I)

to novel compounds of this substance class and also to their use as important precursors or for preparing important precursors for π-conjugated polymers.

11 Claims, No Drawings

PREPARATION OF 2,2'-DI(3,4-ETHYLENEDIOXYTHIOPHENE)S

BACKGROUND OF THE INVENTION

1. Field of the Invention

The invention relates to a process for preparing 2,2'-di (alkylenedioxythiophene)s (also referred to in the literature as 2,2'-bis(3,4-alkylenedioxythiophene)s or 3,4-(alkylene-dioxy)-2,2'-bithiophenes), to novel compounds of this class and also to their use as important precursors or for preparing important precursors for π-conjugated polymers.

2. Brief Description of the Prior Art

The class of the π-conjugated polymers, which are also referred to as conductive polymers or synthetic metals, has been the subject matter of numerous publications. Owing to the considerable delocalization of the π-electrons along the main chain, these polymers exhibit interesting (non-linear) optical properties, and after oxidation or reduction, they become good electrical conductors. This allows these polymers to be used in various practical fields of use, for example in data storage, optical signal processing, the suppression of electromagnetic interference (EMI), solar energy conversion, rechargeable batteries, light-emitting diodes (LEDs), field effect transistors, circuit boards, sensors, capacitors and antistatic materials.

Examples of existing π-conjugated polymers are polypyrroles, polythiophenes, polyanilines, polyacetylenes, polyphenylenes and poly(p-phenylene-vinylenes). A particularly important and industrially utilized polythiophene is poly(3,4-ethylenedioxythiophene) which has very high conductivity in its cationic form. Of note is a series of polymers which contain the 3,4-ethylenedioxythiophene building block, which are suitable as materials for light-emitting diodes, owing to their electroluminescence,.

Of particular interest here are 2,2'-di(3,4-ethylenedioxythiophene) building blocks which are useful for the adjustment of the emission wavelengths and of the luminescence intensity. (See, for example, A. Donat-Bouillud, I. Lévesque, Y. Tao, M. D'Iorio, S. Beaupré, P. Blondin, M. Ranger, J. Bouchard and M. Leclerc, Chem. Mater. 2000, 12, p. 1931–1936).

A problem associated with this use is that the 2,2'-di(3,4-ethylene-dioxythiophene)s have hitherto been obtainable only via complicated organometallic syntheses which, depending on the reaction conditions, can lead to low yields and/or to only moderate purities.

The 2,2'-di(3,4-ethylenedioxythiophene)s have hitherto generally been prepared in the literature by the following process (Ullmann coupling):3,4-Ethylenedioxythiophene is lithiated under protective gas using n-butyllithium at −78° C. in absolute tetrahydrofuran and subsequently coupled with copper(II) chloride oxidatively to give 2,2'-di(3,4-ethylenedioxythiophene).

Pertinent studies cited hereinbelow illustrate the disadvantages of this synthetic route, in particular with regard to reaction conditions, yields and purities: G. A. Sotzing, J. R. Reynolds and P. J. Steel, Adv. Mater. 1997, 9(10), p. 795–798 shows that only an impure product was obtained (m.p. 183–185° C.). A. Donat-Bouillud,. I. Lévesque, Y. Tao, M. D'Iorio S. Beaupré, P. Blondin, M. Ranger, J. Bouchard and M. Leclerc, Chem. Mater. 2000, 12, p. 1931–1936 describe the preparation of a purer product by the same process, (m.p. 203° C.), with yield of only 27.7% of theory, which is rather low. Extension of the reaction time for the Ullmann coupling as reported by A. K. Mohanakrishnan, A. Hucke, M. A. Lyon, M. V. Lakshmikantham and M. P. Cava (Tetrahedron 55 (1999), p. 11745–11754) provided a yield of 84% of a relatively pure product (m.p. 203–204° C.). However, the reaction time had to be increased by a factor of six.

Also, the following significant disadvantages of the processes for preparing 2,2'-di(3,4-ethylenedioxythiophene) are described in all these publications: 1 ) For the lithiation, it is necessary to work at low temperatures (−78° C.) with the aid of an external cold mixture, for example of acetone/dry ice. 2) n-Butyllithium as an organometallic reagent, is expensive and is air- and moisture-sensitive when handled, and also, especially in the event of ingress of moisture, readily flammable. 3) Owing to the sensitivity of the butyl-lithium and of the lithiated thiophene formed as an intermediate, the entire reaction has to be carried out under protective gas (nitrogen or argon).

The variant of this process provided by S. S. Zhu and T. M. Swager in J. Am. Chem. Soc. 1997, 119, p. 12568–12577 (lithiation at −10° C. using tetramethylethylenediamine and oxidative coupling by means of iron(III) acetylacetonate under reflux in THF). This process results in no simplifications, since cold mixtures and protective gas technology are likewise required: The actual yield is 50% of theory (0.99 g of the maximum possible 1.97 g); the 99% reported results from a printing error.

A further significant disadvantage of the cited organometallic procedures is their limited applicability. 2,2'-di(3,4-ethylenedioxythiophene)s substituted on the ethylene bridge have, therefore, hitherto not been described. The substituents can be, for example, hydroxyalkyl groups, carbonyl or heterocarbonyl groups, double bonds, etc. They would not be accessible by a selective route by the method of lithiation with subsequent Ullmann reaction, since, in the case of numerous conceivable substituents on the ethylene bridge, lithiation of these substituents as a side or main reaction would occur. 2,2'-di(3,4-alkylenedioxythiophene)s having alkylene bridges other than the ethylene bridge have also hitherto not been described in the literature.

There is therefore a need for a novel method for preparing existing and also novel 2,2'-di(3,4-alkylenedioxythiophene)s which

- dispenses with the use of low temperatures, i.e. cold mixtures or the like for external cooling,
- allows implementation under air without protective gas technology
- provides broad applicability, for example for the preparation of 2,2'-di(3,4-ethylenedioxythiophene)s functionally substituted on the ethylene bridge or other optionally substituted 2,2'-di(3,4-alkylenedioxythiophene)s.

SUMMARY OF THE INVENTION

According to the invention, this object is achieved by preparing 2,2'-di(3,4-alkylenedioxythiophene)s, which are of the formula (I), in a simple but effective manner by reacting compounds of the general formula (II)

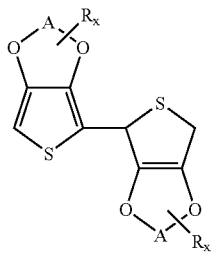

(II)

where

A is an optionally substituted $C_2$–$C_4$-alkylene radical,

R is one or more, identical or different, linear or branched, optionally substituted $C_1$–$C_{18}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s) or one or more hydroxyl radical(s), x is an integer from 0 to 8, with a dehydrogenating agent.

The present invention therefore provides a process for preparing compounds of the general formula (I)

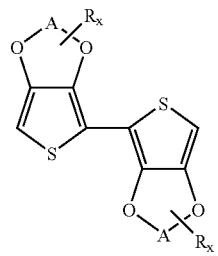

(I)

where

A is an optionally substituted $C_2$–$C_4$-alkylene radical, preferably an optionally substituted substituted ethylene radical, R is one or more, identical or different, linear or branched, optionally substuituted $C_1$–$C_{18}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s) or one or more hydroxyl radical(s), preferably methyl, ethyl, n-propyl, n-butyl, n-hexyl, n-octyl, n-decyl, n-dodecyl, n-tetradecyl or hydroxymethyl, x is an integer from 0 to 8, preferably an integer from 0 to 4, more preferably 0 or 1, characterized in that compounds of the general formula (II)

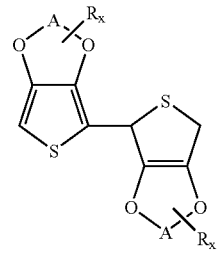

(II)

where A, R and x are each as defined for the compounds of the general formula (I)

are reacted with a dehydrogenating agent.

A preferred embodiment of the process according to the invention is one for preparing the compound of the formula (I-a) (also referred to as 2,2'-di(3,4-ethylenedioxythiophene) of formula (I-a))

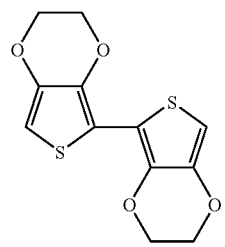

(I-a)

characterized in that compounds of the formula (II-a)

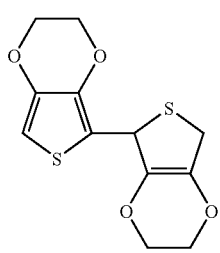

(II-a)

are reacted with a dehydrogenating agent.

Depending on the choice of A and x, the compounds of the formula (II) may include different stereoisomers, i.e. enantiomers or diastereoisomers. For the purposes of the invention, compounds of the formula (II) are either the pure enantiomers or diastereoisomers or mixtures of these in any desired mixing ratio. For example, compounds of the formula (II-a) may be the two enantiomers (II-a-S) or (II-a-R)

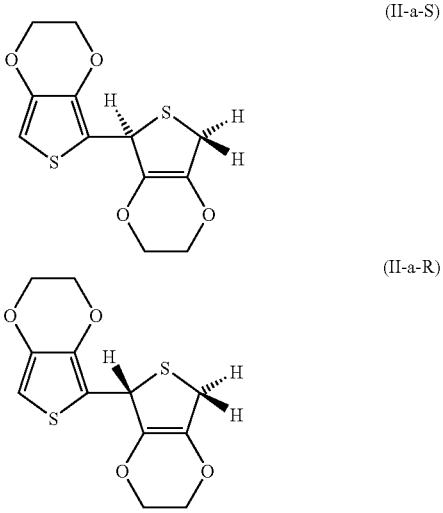

(II-a-S)

(II-a-R)

in pure form or mixtures of these in any desired mixing ratios of (II-a-S) to (II-a-R).

The compounds of the formula (II) can be prepared. by a process which is described in the German patent application DE 10 229 218 which had not yet been published at the priority date of the present application. In the preparation compounds of the formula (VI)

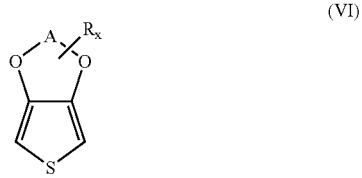

(VI)

where A, R and x are each as defined for general formula (I) are reacted with each other in the presence of Lewis acids, or protic acids. The Lewis acids are preferably nonoxidizing Lewis acids, for example boron trifluoride (for example in the form of the etherate or of another $BF_3$ complex, for example with tetrahydrofuran), antimony pentachloride, aluminium trichloride, titanium tetrachloride, tin tetrachloride and zinc chloride. The protic acids are preferably selected from the group of the sulphonic acids or carboxylic acids, for example p-toluenesulphonic acid, methanesulphonic acid, camphor-10-sulphonic acid or trifluoroacetic acid, or superacids, as a catalyst. The compounds of the general formula (VI) are reacted with the catalyst, for example, in an organic solvent, e.g. halogenated aliphatic hydrocarbons such as methylene chloride or chloroform, alcohols such as methanol or ethanol, or aromatics such as toluene or xylene, at temperatures of 0° C. to 40° C., optionally under protective gas. Preference is given to using from 0.01 to 50% by weight of Lewis acid or 0.5 to 80% by weight of protic acid as the catalyst (% by weight based on the thiophene monomer to be dimerized). The reaction can be carried out for several hours or be followed by $^1$H NMR spectroscopy and terminated at a suitable time by adding bases (e.g. aqueous $Na_2CO_3$ solution) or alcohols (e.g. ethanol). The compounds of the general formula (II) obtained can be purified by column chromatography.

DETAILED DESCRIPTION OF THE INVENTION

The invention is further described by presenting illustrative but non-limiting examples thereof. For the purposes of the invention, $C_2$–$C_4$-alkylene radicals A are ethylene, n-propylene or n-butylene. For the purposes of the invention, linear or branched $C_1$–$C_{18}$-alkyl radicals are, for example, methyl, ethyl, n- or isopropyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl or n-octadecyl. $C_5$–$C_{12}$-cycloalkyl radicals are, for example, cyclopentyl, cyclohexyl, cycloheptyl, cyclooctyl, cyclononyl or cyclodecyl. $C_6$–$C_{14}$-aryl radicals are, for example, phenyl, o-, m-, p-tolyl, benzyl, 2,3-, 2,4-, 2,5-, 2,6-, 3,4-, 3,5-xylyl, mesityl or naphthyl, and $C_1$–$C_4$-hydroxyalkyl radicals are, for example, hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl. Possible substituents of the above-mentioned radicals include numerous organic groups, for example halogen, in particular fluorine, chlorine or bromine, and also ether, thioether, disulphide, sulphoxide, sulphone, aldehyde, keto, carboxylic ester, sulphonic ester, carbonate, cyano, alkylsilane and alkoxysilane groups and/or carboxylamide groups.

Suitable dehydrogenating agents in the process according to the invention are those which are suitable for dehydrogenating 2,3-dihydro-, 2,5-dihydro- or tetrahydrothiophenes and also their derivatives. Preference is given to those which effect a dehydrogenation of the compounds of the general formula (II), but do not support any subsequent oxidative polymerization of the compounds of the general formula (I) obtained. The dehydrogenation results in an aromatization of the dihydrothiophenes or compounds of the general formula (II). For the purposes of the invention, the dehydrogenation can be conducted by various routes:

by thiolation and elimination of hydrogen sulphide by hydride ion transfer by halogenation by means of halogenating reagents and elimination of hydrogen halide by S-oxidation by means of suitable oxidizing agents and dehydration.

Dehydrogenating agents used in the process according to the invention are for example and with preference quinones, sulphur, bromine; N-bromo- or N-chlorosuccinimide, sulphuryl chloride, hydrogen peroxide or hypervalent iodine compounds such as iodosobenzene. The dehydrogenation with quinones results in direct hydrogenation of the dehydrogenating agent used (hydride ion transfer). The use of, for example, bromine, N-bromo- or N-chlorosuccinimide or sulphuryl chloride results in a halogenation and subsequent elimination of hydrogen halide, hydrogen peroxide or iodosobenzene. This effects an S-oxidation followed by a dehydration, and sulphur effects thiolation followed by an elimination of hydrogen-sulphide. Such reactions are described in Houben-Weyl, *Methoden der Organischen Chemie* (4$^{th}$ ed., Volume E 6a (Hetarenes I, part 1), publ. R. P. Kreher, Georg Thieme-Verl., Stuttgart-New York 1994, in the chapter "Thiophenes" (author: W. -D. Rudorf) on pages 370 to 388 in sections 3. 3. to 3. 8.).

Particularly preferred dehydrogenating agents for use in the process according to the invention are quinones, and very particular preference among these is given to 2,3,5,6-tetrachloro-1,4-benzoquinone (chloranil) or 2,3-dichloro-5,6-dicyano-1,4-benzoquinone.

The process according to the invention is in principle carried out in such a way that the compounds of the general formula (II) are reacted with at least equimolar or excess amounts of dehydrogenating agent at a suitable temperature and optionally in an organic solvent for 0.5 to 48 h, preferably 2 to 24 h. For 1 mol of the compound of the general formula (II), preference is given to using 1 to 2 mol, particular preference to 1 to 1.2 mol, of dehydrogenating agent, and in many cases a precisely equimolar ratio between the compound of the general formula (II) used and dehydrogenating agent is sufficient. Any precipitated solid is filtered off and freed of insoluble constituents by slurrying and subsequently filtering. Suitable for slurrying is, for example, a mixture of organic solvent and aqueous alkali solution, e.g. 4% aqueous KOH solution. After basic washing and subsequent washing to neutrality with water of both this resulting mother liquor and the mother liquor which has been obtained after filtration of the reaction mixture, the mother liquors are concentrated. and dried under reduced pressure. Likewise suitable for basic washing are aqueous alkali solutions, e.g. 4% aqueous KOH solution., The resulting crude product can be purified by common methods, for example column chromatography or by recrystallization; also suitable for this purpose is the removal of strongly colouring impurities with bleaching earth (montmorillonite), e.g. Tonsil®, available from Süd-Chemie, Munich.

Suitable reaction temperatures for carrying out the process according to, the invention are, for example, 20 to 200° C., preferably 100 to 170° C., and it may be advantageous to work with reflux of the solvent used. As would be realized while one can in principle employ lower temperatures of 20° C. down to −78° C., in carrying out the process of the invention, at the lower temperatures would be attended by costly and inconvenient external cooling or use of cold mixtures. Suitable solvents are, for example, optionally halogenated aromatic hydrocarbons such as toluene, xylene, chlorobenzene or o-dichlorobenzene. However, it is also possible to use further preferably organic solvents which are inert under the reaction conditions, optionally in a mixture with water.

The process according to the invention for the first time provides compounds of the general formula (I) which may be substituted on the ethylene bridge and even those which bear optionally substituted alkylene bridges other than the ethylene bridge. Such compounds of the formula (I) have hitherto not been described in the literature.

The present invention therefore likewise provides compounds of the general formula (I)

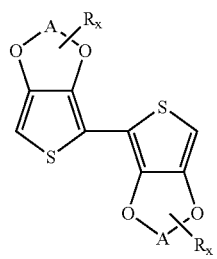

(I)

where

A, R and x are each as defined above, excluding the compound of the formula (I-a)

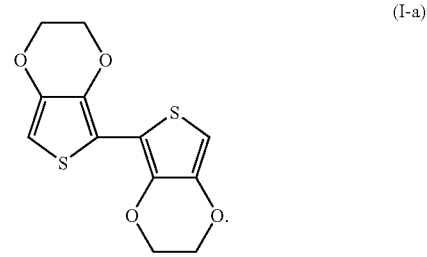

(I-a)

For the purposes of the invention, compounds of the general formula (I) where, for example, A is an ethylene radical and x=1 may be one of the three constitutional isomers in pure form

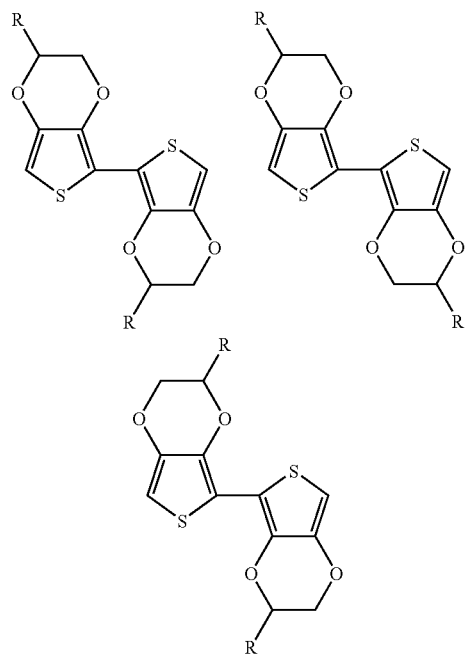

or mixtures of these in any desired mixing ratios. In addition, the different constitutional isomers may occur in different stereoisomeric forms which, for the purposes of the invention, likewise in pure form or as mixtures in any desired mixing ratios, are compounds of the general formula (I). This is likewise true for compounds of the general formula (I) in which A and/or x have a meaning other than ethylene (A) or 1 (x), when different isomers are structurally possible.

The compounds of the general formula (I) are suitable either as precursors or for preparing valuable precursors in the preparation of π-conjugated, electrically conducting or semiconducting polymers or other electrically conducting or semiconducting compounds.

The present invention therefore further provides the use of the compounds of the general formula (I) as precursors or for preparing precursors for the preparation of electrically conducting or semiconducting compounds and/or polymers. In this context, polymers, in addition to homopolymers, also include π-conjugated, electrically conducting or semiconducting copolymers which, in addition to monomer units of the general formula (V)

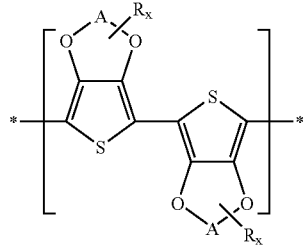

(V)

contain further monomer units, for example optionally substituted fluorene, thiophene, furan, pyrrole, aniline, pyridine, carbazole or phenylene units.

In this context, electrically conducting or semiconducting compounds are, for example, optionally substituted π-conjugated oligomers containing at least four identical or different (hetero)arylene units, for example fluorene, thiophene, furan, pyrrole, aniline, pyridine, carbazole or phenylene units, containing at least one monomer unit of the general formula (V) (corresponding to two (hetero)arylene units). Those skilled in the art of semiconductors are also familiar with such compounds as "small molecules".

The present invention preferably provides the use of the inventively prepared or inventive compounds of the general formula (I) for preparing electrically conducting or semiconducting poly(3,4-ethylenedioxythiophenes) or for preparing 5,5'-dihalo-2,2'-di-(3,4-alkylenedioxythiophene)s.

The inventively prepared compounds of the general formula (I) can be converted, for example, by oxidative polymerization, for example using iron(III) compounds as an oxidizing agent, to the corresponding poly(3,4-ethylenedioxythiophenes) which find a variety of uses as conducting or semiconducting polymers.

The present invention therefore also provides a process for preparing neutral or cationic compounds of the general formula (IV)

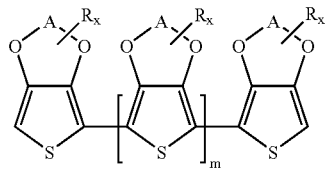

(IV)

where
A, R and x are as defined above,
m is an even integer from 2 to 200 and in the case that the compounds of the general formula (IV) are cationic, they bear a positive charge from at least one up to at most m+2, characterized in that compounds of the general formula (I)

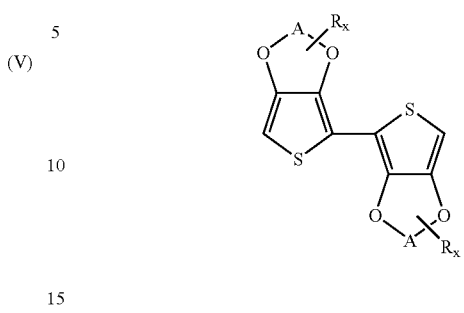

(I)

where
A, R and x are as defined above, are oxidatively polymerized by chemical or electrochemical means.

The polythiophenes of the general formula (IV) may be neutral or cationic. In the case that the polythiophenes are cationic, the positive charges of the polythiophene polycations are not represented in the formula (IV), since their precise number and position cannot be precisely determined. However, the number of positive charges is at least 1 and at most m+2.

To balance the positive charge, the cationic form of the polythiophenes contains anions, preferably polyanions, as counterions.

The polyanions are preferably the anions of polymeric carboxylic acids such as polyacrylic acids, polymethacrylic acid or polymaleic acids, and polymeric sulphonic acids such as polystyrenesulphonic acids and polyvinylsulphonic acids. These polycarboxylic and -sulphonic acids may also be copolymers of vinylcarboxylic and vinylsulphonic acids with other polymerizable monomers such as acrylic esters and styrene.

Particular preference is given to the anion of polystyrenesulphonic acid as the counterion.

The molecular weight of the polyacids affording the polyanions is preferably 1 000 to 2 000 000, more preferably 2 000 to 500 000. The polyacids or their alkali metal salts are commercially available, for example polystyrenesulphonic acids and polyacrylic acids.

The compounds of the general formula (I) according to the invention can be converted oxidatively to polythiophenes of the general formula (IV) by chemical or electrochemical means. The method both of oxidative chemical and electrochemical polymerization of polythiophenes or 3,4-alkylenedioxythiophene derivatives is known to those skilled in the art and described in detail in the literature (L. Groenendaal, F. Jonas, D. Freitag, H. Pielartzik and J. R. Reynolds, Adv. Mater. 2000, 12(7), p.481–494). Suitable chemical oxidizing agents are those known from the prior art for polythiophene preparation, for example iron(III) compounds such as $FeCl_3$ or iron(III) tosylate, potassium permanganate, manganese dioxide ($MnO_2$), potassium (di)chromate or peroxodisulphates (persulphates), such as $Na_2S_2O_8$ or $K_2S_2O_8$, and also $H_2O_2$.

The inventively prepared or inventive compounds can also be converted by halogenation, preferably chlorination or bromination, to compounds of the general formula (III) (also referred to as 5,5'-dihalo-2,2'-di-(3,4-alkylenedioxythiophenes)) which are valuable precursors in the transition metal-catalysed preparation of π-conjugated polymers. The process in principle is known to those skilled in the art and described, for example, in A. Donat-Bouillud, I. Lévesque, Y. Tao, M. D'Iorio, S. Beaupré, P. Blondin, M. Ranger, J. Bouchard and M. Leclerc, Chem. Mater. 2000, 12, p. 1931–1936.

The present invention therefore further provides a process for preparing compounds of the general formula (III)

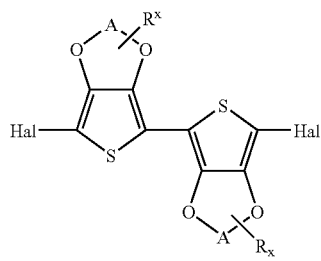
(III)

where
A, R and x are each as defined above and
Hal is Cl or Br, excluding the compound of the formula (III-a)

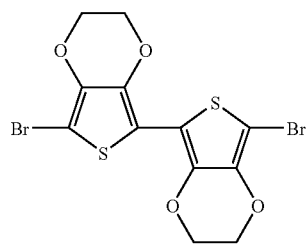
(III-a)

characterized in that compounds of the general formula (I)

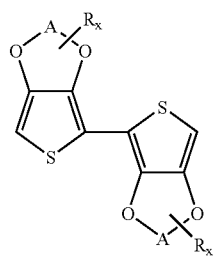
(I)

where
A, R and x as defined above, are halogenated.

This and other aspects of the invention are further described by the following illustrative but non-limiting examples.

EXAMPLES

General Method for Synthesizing the Compounds of the General Formula (II):

For example, the compounds of the general formula (II) can be synthesized by reacting a solution of the 3,4-alkylenedioxythiophene in methylene chloride with 0.5 to 80% by weight of a protic acid, for example p-toluenesulphonic acid or trifluoroacetic acid, or 0.01 to 50% by weight of a Lewis acid, for example boron trifluoride in the form of the etherate or of another $BF_3$ complex, as a catalyst, at temperatures of 0° C. to 40° C., optionally under an $N_2$ atmosphere. The conversion can be carried out for several hours or followed by $^1H$ NMR spectroscopy and terminated at a suitable time by adding bases (e.g. aqueous $Na_2CO_3$ solution) or alcohols (e.g. ethanol). The resulting compounds of the general formula (II) can subsequently be purified by column chromatography, for example on silica gel using methylene chloride as the eluent.

Preparation of 2,2',3,3',5,7-Hexahydro-5,5'-Bithieno[3,4-b][1,4]Dioxin (II-a) (EDT Dimer) by Trifluoroacetic Acid catalysis

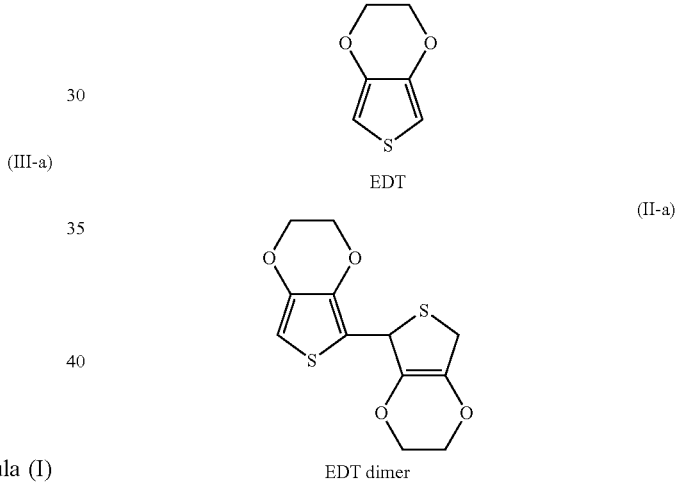

As described in the general method, 2.13 g of trifluoroacetic acid in 90 ml of methylene chloride were added at 18° C. to a solution of 42.6 g (0.3 mol) of 3,4-ethylenedioxythiophene (EDT) in 70 ml of methylene chloride. The reaction mixture was stirred at 18° C. under an $N_2$ atmosphere for 48 h. Afterwards, the reaction was stopped by vigorous stirring with 150 ml of aqueous 5% $Na_2CO_3$ solution. The organic phase was removed, washed to neutrality with water and freed of solvent at 20 mbar on a rotary evaporator. The residue (42.2 g) was separated by column chromatography on silica gel using methylene chloride as the eluent.

Fraction 1: 21 g of EDT
Fraction 2: 11 g of EDT dimer, identified by means of $^1H$ NMR in $CDCl_3$. Beige crystals,
m.p.: 115–119 ° C.
Fraction 3: 1 g of EDT trimer as an isomer mixture, identified by means of $^1H$ NMR in $CDCl_3$. Beige crystals.

The product from fraction 2 was used in the inventive examples 1 and 2.

Preparation of Dimethyl-2,2',3,3',5,7-Hexahydro-5, 5'-Bithieno[3,4-b][1,4]Dioxin (II-b) (Methyl-EDT Dimer) by BF$_3$ Catalysis

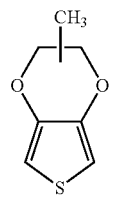

Methyl-EDT

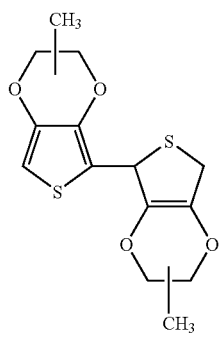

(II-b)

As described in the general method, 0.24 ml of boron trifluoride etherate (corresponding to 269 mg=1.89 mmol) in 40 ml of methylene chloride was added at 23° C. to a solution of 6.25 g (40 mmol) of 2-methyl-2,3-dihydrothieno [3,4-b][1,4]dioxin (methyl-EDT) in 30 ml of methylene chloride. The reaction mixture was stirred at 23° C. under an N$_2$ atmosphere for 7 h. Afterwards, the reaction was stopped by adding 20 ml of ethanol. The organic phase was washed to neutrality with water and freed of solvent at 20 mbar on a rotary evaporator. The residue was separated by column chromatography on silica gel using methylene chloride as the eluent. Yield: 1.3 g of methyl-EDT dimer (II-b) (20.8% of theory).

Preparation of [(Hydroxymethyl)-2,2',3,3',5,7-Hexahydro-5,5'-Bithieno[3,4-b][1,4]Dioxinyl]methanol (II-c) (hydroxymethyl-EDT Dimer)

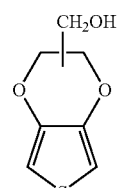

EDT-Methanol

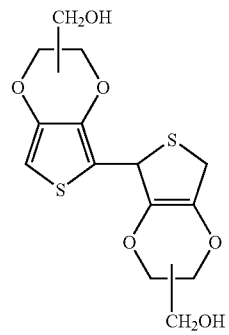

(II-c)

As described in the general method, 0.24 ml of boron trifluoride etherate (corresponding to 269 mg=1.89 mmol) in 120 ml of methylene chloride were added at 0° C. to a solution of 6.89 g (40 mmol) of 2,3-dihydrothieno[3,4-b][1, 4]dioxin-2-ylmethanol (hydroxymethyl-EDT, "EDT methanol") in 90 ml of methylene chloride. The reaction mixture was stirred at 0° C. under an N$_2$ atmosphere for 4 h. Afterwards, the reaction was stopped by adding a mixture of 60 ml of ethanol/120 ml of water. The organic phase was removed and freed of solvent at 20 mbar on a rotary evaporator. The residue was separated by column chromatography on silica gel using methylene chloride as the eluent. Yield: 2.0 g of hydroxymethyl-EDT dimer (II-c) (29% of theory).

Example 1

Preparation of 2,2'-Di(3,4-Ethylenedioxythiophene) (I-a) (Inventive)

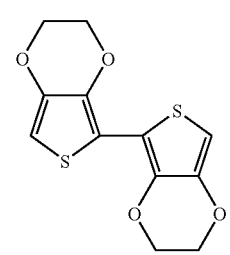

(I-a)

28.64 g (0.1 mol) of EDT dimer (II-a) were dissolved in 500 ml of xylene. 24.59 g (0.1 mol) of chloranil were added to this solution. The mixture was heated to reflux at 140° C. for 10 h. After cooling, the precipitated crystals were filtered off with suction and both the crystals and the mother liquor were worked up further.

The mother liquor was washed 4 times with 50 ml each time of 4% potassium hydroxide solution and finally washed to neutrality with water. The solution was concentrated by evaporation and dried under high vacuum; 15.8 g of crude product were obtained as green crystals (fraction A).

The crystals which had been filtered off with suction were slurried with 150 ml of xylene and 100 ml of 4% strength potassium hydroxide solution and the insoluble fractions (5.5 g) were filtered off. The mother liquor was worked up in the same way as the above mother liquor and, after concentration by evaporation, provided a further 6.4 g of crude product as green crystals (fraction B).

The crude products (fractions A and B) were dissolved in 370 ml of methylene chloride and slurried with 21 g of Tonsil® (bleaching earth of the montmorillonite type, manufacturer: Sud-Chemie, Munich). After decolorizing the solution, the Tonsil® was filtered off and the methylene chloride removed on a rotary evaporator.

18 g (63% of theory) of 2,2'-di(3,4-ethylenedioxythiophene) (I-a) are isolated as bright yellow crystals. m.p.: 204–205° C.

$^1$H NMR spectrum (400 MHz, CDCl$_3$, ppm): 4.24 (4H, m), 4.31 (4H, m), 6.27 (2H, s).

Slurrying of the 5.5 g of insoluble fractions with Tonsil® in methylene chloride by the same method provided a further 1.5 g of 2,2'-di(3,4-ethylenedioxythiophene). Total yield: 69% of theory.

Example 2

Preparation of 2,2'-Di(3,4-Ethylenedioxythiophene) (I-a) with 2,3-Dichloro-5,6-Dicyano-p-Benzoquinone 8.53 g (30 mmol) of EDT dimer (II-a) were dissolved in 150 ml of xylene. 7.15 g (31.5 mmol)-of 2,3-dichloro-5,6-dicyano-p-benzoquinone were added to this solution. The mixture was heated to reflux at 140° C. for 24 h. After cooling, the mixture was extracted using 4% potassium hydroxide solution until the potassium hydroxide solution remained colourless. Finally, the mixture was washed to neutrality with water. The solution was concentrated by evaporation and dried in high vacuum; 3.68 g (43.5% of theory) of crude product were obtained as a grey-brown residue. This crude product was purified by chromatography on a silica gel column, methylene chloride eluent.

1.32 g (15.6% of theory) of pure 2,2'-di(3,4-ethylenedioxythiophene) (I-a) were isolated. m.p.: 207–209° C.

The $^1$H NMR spectrum (400 MHz, CDCl$_3$) is identical to that reported in Example 1.

Example 3

Preparation of Dimethyl-2,2',3,3'-Tetrahydro-5,5'-Bithieno[3,4-b][1,4]Dioxin (I-b)

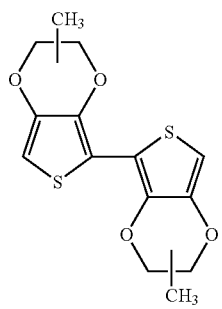

(I-b)

0.85 g (2.7 mmol) of methyl-EDT dimer (II-b) was dissolved in 50 ml of xylene. 0.668 g (2.7 mmol) of chloranil was added to this solution. The mixture was heated to reflux at 140° C. for 14 h. After cooling, the mixture was diluted with methylene chloride and extracted with 4% potassium hydroxide solution until the potassium hydroxide solution remained colourless. Finally, the mixture was washed to neutrality with water. The solution was concentrated by evaporation and dried under high vacuum; 0.48 g (56.7% of theory) of crude (I-b) was obtained as the residue. The product was purified by column chromatography on silica gel, CH$_2$Cl$_2$ eluent. Pure yield 0.38 g (44.8% of theory).

$^1$H NMR spectrum (400 MHz, CDCl$_3$, ppm): 6.24, 6.235, 6.23 (3 s, together 2H); 4.39 (q with further splitting, $^3$J=6.56 Hz) and 4.32 (q with further splitting, $^3$J=6.56 Hz, both q together 2H); 4.28 (dd, $^2$J=11.60 Hz, $^3$J=2.04 Hz) and 4.15 (dd, $^2$J=11.60 Hz, $^3$J=2.04 Hz, both dd together 2 H); 3.91 (dd, $^2$J=11.60 Hz, $^3$J=8.56 Hz) and 3.865 (dd, $^2$J=11.60 Hz, $^3$J=8.56 Hz, both dd together 2H); 1.42 (d, $^3$J=6.56 Hz) and 1.355 (d, $^3$J=6.56 Hz, both d together 6H). The NMR spectrum suggests the presence of a product mixture of the following components:

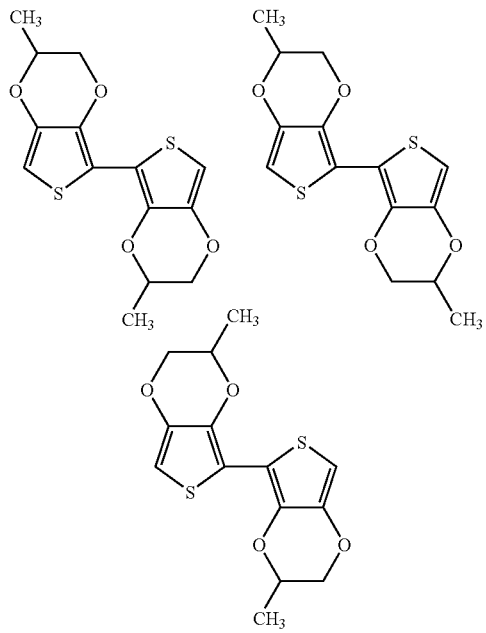

Example 4

Preparation of [(Hydroxymethyl)-2,2',3,3'-Tetrahydro-5,5'-Bithieno[3,4-b][1,4]Dioxinyl]Methanol (I-c)

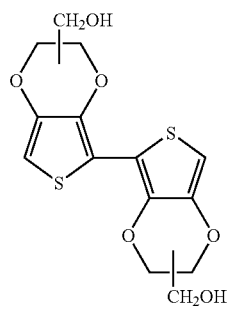

(I-c)

2.4 g (7 mmol) of hydroxymethyl-EDT dimer (II-c) were dissolved in 50 ml of xylene. 1.713 g (7 mmol) of chloranil were added to this solution. The mixture was heated to reflux at 140° C. for 24 h. After cooling, the mixture was extracted using 4% potassium hydroxide solution until the potassium hydroxide solution remained colourless. Finally, the solution was washed to neutrality with water. The solution was concentrated by evaporation and dried under high vacuum; 0.2 g (8.3% of theory) of (I-c) was obtained as the residue.

$^1$H NMR spectrum (400 MHz, CDCl$_3$, ppm): 6.285; 6.275; 6.27; 6.26 (4 s, together 2H), 4.21–3.73 (several m, together 6H). The NMR spectrum suggests the presence of a product mixture of the following components:

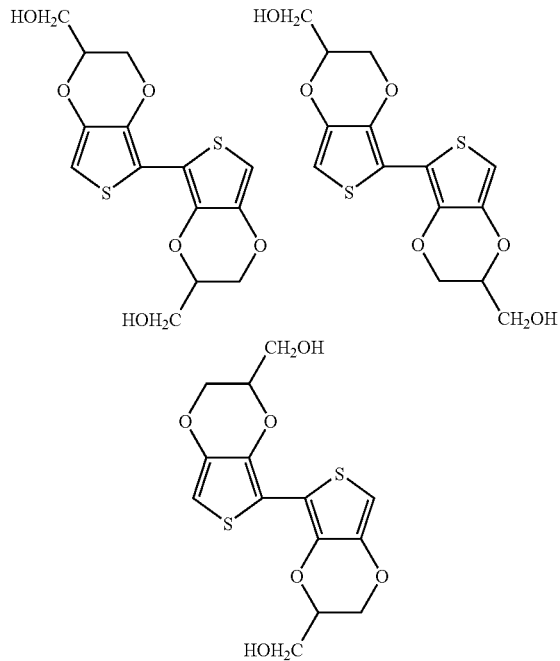

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing compounds of the general formula (I)

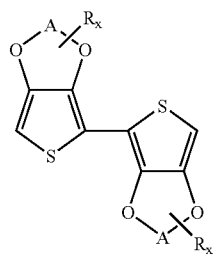

(I)

where

A is an optionally substituted C$_2$–C$_4$-alkylene radical,

R is one or more, identical or different, linear or branched, optionally substuituted C$_1$–C$_{18}$-alkyl radical(s), optionally substituted C$_5$–C$_{12}$-cycloalkyl radical(s), optionally substituted C$_6$–C$_{14}$-aryl radical(s), optionally substituted C$_1$–C$_4$-hydroxyalkyl radical(s) or one or more hydroxyl radical(s), x is an integer from 0 to 8, comprising reacting compounds of the general formula (II)

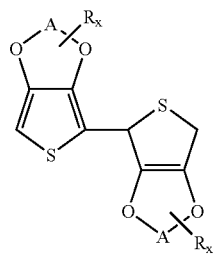

(II)

where

A, R and x are each as defined for the compounds of the general formula (I)

with a dehydrogenating agent.

2. Process according to claim 1, characterized in that

A is an optionally substituted ethylene radical,

R is one or more, identical or different, linear or branched, optionally substuituted C$_1$–C$_{18}$-alkyl radical(s), optionally substituted C$_5$–C$_{12}$-cycloalkyl radical(s), optionally substituted C$_6$–C$_{14}$-aryl radical(s), optionally substituted C$_1$–C$_4$-hydroxyalkyl radical(s) or one or more hydroxyl radical(s), x is an integer from 0 to 4.

3. Process according to claim 1 characterized in that

A is an optionally substituted ethylene radical,

R is methyl, ethyl, n-propyl, n-butyl, n-hexyl, n-octyl, n-decyl, n-dodecyl, n-tetradecyl or hydroxymethyl, x is 0 or 1.

4. Process according to claim 1 for preparing the compound of the formula (I-a)

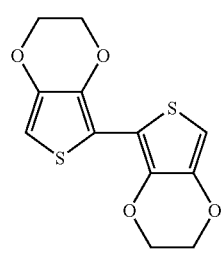

(I-a)

comprising reacting compounds of the formula (II-a)

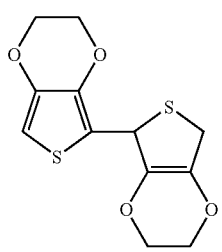

(II-a)

with a dehydrogenating agent.

5. Process according to claim 1, characterized in that the dehydrogenating agent is selected from the group of the quinones, sulphur, bromine, N-chloro- or N-bromosuccinimide, sulphuryl-chloride, hydrogen peroxide and iodosobenzene.

6. Process according to claim 1, characterized in that the dehydrogenating agent is a quinone.

7. Process according to claim 1 characterized in that the dehydrogenating agent is 2,3,5,6-tetrachloro-1,4-benzoquinone (chloranil) or 2,3-dichloro-5,6-dicyano-1,4-benzoquinone.

8. Compounds of the general formula (I)

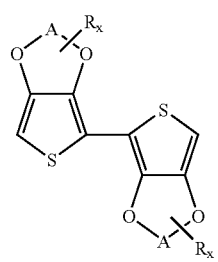
(I)

where
A, R and x are each as defined in claim 1, excluding the compound of the formula (I-a)

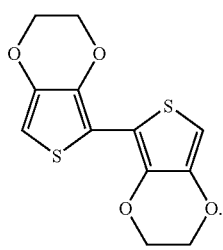
(I-a)

9. A process for preparing electrically conducting or semiconducting compounds and/or electrically conducting or semiconducting polymers comprising providing the compounds according to claim 8 as a precursor.

10. Process for preparing compounds of the general formula (III)

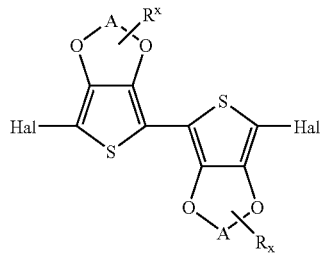
(III)

where
A, R and x are each as defined in claim 1 and
Hal is Cl or Br, excluding the compound of the formula (III-a)

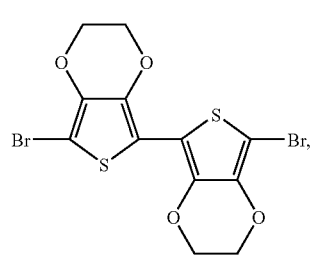
(III-a)

comprising halogenating compounds of the general formula (I)

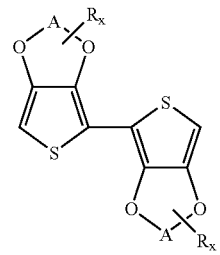
(I)

where
A, R and x are each as defined in claim 1.

11. Process for preparing neutral or cationic compounds of the general formula (IV)

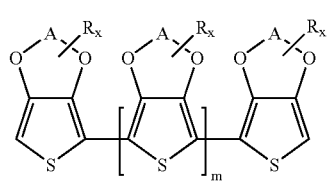
(IV)

where
A, R and x are each as defined in claim 1,
m is an even integer from 2 to 200 and
in the case that the compounds of the general formula (IV) are cationic, they bear a positive charge from at least one up to at most m+2,
comprising oxidatively polymerizing compounds of the general formula (I)

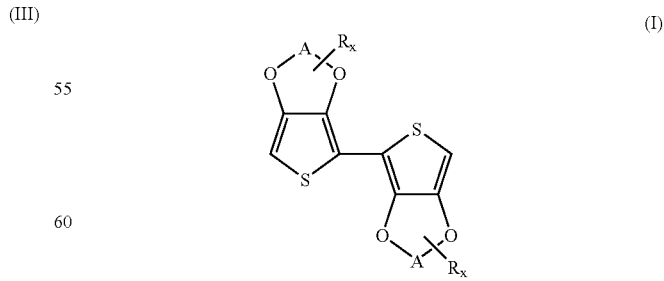
(I)

where
A, R and x are each as defined in claim 1.

* * * * *